United States Patent [19]
Nikiforov et al.

[11] Patent Number: 5,610,287
[45] Date of Patent: Mar. 11, 1997

[54] METHOD FOR IMMOBILIZING NUCLEIC ACID MOLECULES

[75] Inventors: Theo Nikiforov, San Diego, Calif.; Michael R. Knapp, Baltimore, Md.

[73] Assignee: Molecular Tool, Inc., Baltimore, Md.

[21] Appl. No.: 341,148

[22] Filed: Nov. 16, 1994

Related U.S. Application Data

[63] Continuation-in-part of Ser. No. 162,397, Dec. 6, 1993, abandoned.

[51] Int. Cl.$^6$ ............... C07H 21/04; C12Q 1/68; C12N 15/00; C12N 11/08
[52] U.S. Cl. ............... 536/24.3; 435/6; 435/172.3; 435/180; 536/24.31; 536/24.32; 536/24.33; 536/25.3
[58] Field of Search ............... 435/180, 6, 172.3; 536/24.3, 24.31, 24.32, 25.3, 24.33

[56] References Cited

U.S. PATENT DOCUMENTS

| | | | |
|---|---|---|---|
| 4,656,127 | 4/1987 | Mundy et al. | 435/6 |
| 5,104,791 | 4/1992 | Abbott et al. | 435/6 |
| 5,221,518 | 6/1993 | Mills | 422/62 |

FOREIGN PATENT DOCUMENTS

| | | | |
|---|---|---|---|
| WO92/15712 | 4/1992 | WIPO | C12Q 1/68 |

OTHER PUBLICATIONS

Nagata et al., "Quantification of picogram levels of specific DNA immobilizd in microliter wells," *FEBS Letters* 183:379–382 (1985).

Dahlen, P. et al., "Sensitive detection of genes by sandwich hybridization and time–resolved fluorometry," *Mol. Cell. Probes* 1:159–168 (1987).

Keller, G. H. et al., "Detection of Human Immunodeficiency Virus Type 1 DNA by Polymerase Chain Reaction Amplification and Capture Hybridization in Microliter Wells," *J. Clin. Microbiol.* 29:638–641 (1991).

Holstrom, K. et al., "A Highly Sensitive and Fast Nonradioactive Method for Detection of Polymerase Chain Reaction Products," *Anal. Biochem.* 209:278–283 (1993).

Running, J. A. et al., "A Procedure for Productive Coupling of Sythetic Oligonucleotides to Polystyrene Microtiter Wells for Hybridization Capture," *BioTechniques* 8:276–277 (1990).

Newton, C. R. et al., "The production of PCR products with 5–prime single–stranded tails using primers that incorporate novel phosphoramidite intermediates," *Nucl. Acids Res.* 21:1155–1162 (1993).

Rasmussen, S. R. et al., "Covalent Immobolization of DNA onto Polystyrene Microwells: The Molecules Are Only Bound at the 5–prime End," *Anal. Biochem.* 198:138–142 (1991).

Varga, J. M. et al., "Immobilization of small molecules and proteins by radio–derivatized polystyrene," *FASEB* 4:2671–2677 (1990).

Lacy, M. J. et al., "Direct absorbtion of ssDNA to polystyrene for characterization of the DNA/anti–DNA interaction, and immunoassay for anti–DNA autoantibody in New Zealand White mice," *J. Immunol. Methods* 116:87–98 (1989).

Ranki et al., "Sandwich hybridization as a convenient method for the detection of nucleic acids in crude samples", *Gene* 21:77–85 (1983).

Urdea et al., "A novel method for the rapid detection of specific nucleotide sequences in crude biological samples without blotting or radioactivity; application to the analysis of hepatitis B virus in human serum," *Gene* 61:253–264 (1987).

*Primary Examiner*—David M. Naff
*Attorney, Agent, or Firm*—Howrey & Simon; Jeffrey I. Auerbach

[57] ABSTRACT

Synthetic nucleic acid molecules are non-covalently immobilized in the presence of a salt or cationic detergent on a hydrophilic polystyrene solid support containing an —OH, —C=O or —COOH hydrophilic group or on a glass solid support. The support is contacted with a solution having a pH of about 6 to about 8 containing the synthetic nucleic acid and the cationic detergent or salt. Preferably, the cationic detergent is 1-ethyl-3-(3'-dimethylaminopropyl)-1,3-carbodiimide hyrochloride at a concentration of about 30 mM to about 100 mM or octyldimethylamine hydrochloride at a concentration of about 50 mM to about 150 mM. The salt is preferably NaCl at a concentration of about 50 mM to about 250 mM. When the detergent is 1-ethyl-3-(3'-dimethylaminopropyl)-1,3-carbodiimide hyrochloride, the glass support or the hydrophilic polystyrene support is used. When NaCl or octyldimethylamine hydrochloride is used, the support is the hydrophilic polystyrene. After immobilization, the support containing the immobilized nucleic acid may be washed with an aqueous solution containing a non-ionic detergent. The immobilized nucleic acid may be used in nucleic acid hybridization assays, nucleic acid sequencing and in analysis of genomic polymorphisms.

19 Claims, 4 Drawing Sheets

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Equus caballus ( v i i ) IMMEDIATE SOURCE:
( B ) CLONE: 1129

( x i ) SEQUENCE DESCRIPTION: SEQ ID NO:1:

ACCAGGCACC ACGCGGTCTG AGGCT   25

( 2 ) INFORMATION FOR SEQ ID NO:2:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Equus caballus ( v i i ) IMMEDIATE SOURCE:
  ( B ) CLONE: Biotin-T25

( x i ) SEQUENCE DESCRIPTION: SEQ ID NO:2:

TTTTTTTTTT TTTTTTTTTT TTTTT                         25

( 2 ) INFORMATION FOR SEQ ID NO:3:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Equus caballus ( v i i ) IMMEDIATE SOURCE:
  ( B ) CLONE: 1112

( x i ) SEQUENCE DESCRIPTION: SEQ ID NO:3:

AGTATAATAA TCACAGTATG TTAGC                         25

( 2 ) INFORMATION FOR SEQ ID NO:4:

( i ) SEQUENCE CHARACTERISTICS:
  ( A ) LENGTH: 35 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Equus caballus ( v i i ) IMMEDIATE SOURCE:
  ( B ) CLONE: 1676

( x i ) SEQUENCE DESCRIPTION: SEQ ID NO:4:

CCACGGGTAA CATACTGTGA TTATTATACT TAGAT               35

( 2 ) INFORMATION FOR SEQ ID NO:5:

( i ) SEQUENCE CHARACTERISTICS:
  ( A ) LENGTH: 25 base pairs
  ( B ) TYPE: nucleic acid
  ( C ) STRANDEDNESS: single

5,610,287

27

28

-continued ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Equus caballus ( v i i ) IMMEDIATE SOURCE:
                ( B ) CLONE: 308

( x i ) SEQUENCE DESCRIPTION: SEQ ID NO:5:

AGCCTCAGAC CGCGTGGTGC CTGGT                                              25

( 2 ) INFORMATION FOR SEQ ID NO:6:

( i ) SEQUENCE CHARACTERISTICS:
                ( A ) LENGTH: 25 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Equus caballus ( v i i ) IMMEDIATE SOURCE:
                ( B ) CLONE: 680

( x i ) SEQUENCE DESCRIPTION: SEQ ID NO:6:

GAGATTCAGC TCTAAGTGCT GTGGG                                              25

( 2 ) INFORMATION FOR SEQ ID NO:7:

( i ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Equus caballus ( v i i ) IMMEDIATE SOURCE:
                ( B ) CLONE: 1209

( x i ) SEQUENCE DESCRIPTION: SEQ ID NO:7:

TGCAGCCCAC AGCACTTAGA GCTGAATCTC                                         30

( 2 ) INFORMATION FOR SEQ ID NO:8:

( i ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO (iv) ANTI-SENSE: NO (vi) ORIGINAL SOURCE:
  (A) ORGANISM: Equus caballus (vii) IMMEDIATE SOURCE:
  (B) CLONE: 1210

(xi) SEQUENCE DESCRIPTION: SEQ ID NO:8:

TGCAACCCAC AGCACTTAGA GCTGAATCTC                          30

(2) INFORMATION FOR SEQ ID NO:9:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Equus caballus (xi) SEQUENCE DESCRIPTION: SEQ ID NO:9:

CCAAAGGAGC TGGGTCTGAA ACAAA                               25

(2) INFORMATION FOR SEQ ID NO:10:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Equus caballus (xi) SEQUENCE DESCRIPTION: SEQ ID NO:10:

ATGGCTTCCC ACCCTACCCA TCCCG                               25

(2) INFORMATION FOR SEQ ID NO:11:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Equus caballus (xi) SEQUENCE DESCRIPTION: SEQ ID NO:11:

TGTTCTGGGA AAGACCACAT TATTT                               25

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equus caballus ( x i ) SEQUENCE DESCRIPTION: SEQ ID NO:12:

ATGCTCCCAG GTGATTCCAG TGTGC        25

( 2 ) INFORMATION FOR SEQ ID NO:13:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equus caballus ( x i ) SEQUENCE DESCRIPTION: SEQ ID NO:13:

GGTGCTGTGC GAGGTACACT TGACTG        26

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equus caballus ( x i ) SEQUENCE DESCRIPTION: SEQ ID NO:14:

AGAAACACAA GGCCCAAGAA CAGGA        25

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO (vi) ORIGINAL SOURCE:
    (A) ORGANISM: Equus caballus (xi) SEQUENCE DESCRIPTION: SEQ ID NO:15:

GGATCCAGAT GAACAACCAG ATGAA 25

(2) INFORMATION FOR SEQ ID NO:16:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Equus caballus (xi) SEQUENCE DESCRIPTION: SEQ ID NO:16:

CTGCAGCCCA CTGGGCCTTC TTTGT 25

(2) INFORMATION FOR SEQ ID NO:17:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Equus caballus (xi) SEQUENCE DESCRIPTION: SEQ ID NO:17:

CCTTTGTGTA GAGTAGTTCA AGGAC 25

(2) INFORMATION FOR SEQ ID NO:18:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Equus caballus (vii) IMMEDIATE SOURCE:
       (B) CLONE: 1833

(xi) SEQUENCE DESCRIPTION: SEQ ID NO:18:

ATAATACAGA AGTTCTGAGA GGCTA 25

(2) INFORMATION FOR SEQ ID NO:19:

(i) SEQUENCE CHARACTERISTICS:

(A) LENGTH: 25 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: NO (v i) ORIGINAL SOURCE:
  (A) ORGANISM: Equus caballus (v i i) IMMEDIATE SOURCE:
  (B) CLONE: 1834

(x i) SEQUENCE DESCRIPTION: SEQ ID NO:19:

GGATCCAGGT CTGCTTCTGC TTCCC   25

(2) INFORMATION FOR SEQ ID NO:20:

(i) SEQUENCE CHARACTERISTICS:
  (A) LENGTH: 25 base pairs
  (B) TYPE: nucleic acid
  (C) STRANDEDNESS: single
  (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
  (A) ORGANISM: Equus caballus (v i i) IMMEDIATE SOURCE:
  (B) CLONE: 814

(x i) SEQUENCE DESCRIPTION: SEQ ID NO:20:

AAGAGAAAGA GTTTTGCCTC AATCC   25

(2) INFORMATION FOR SEQ ID NO:21:

(i) SEQUENCE CHARACTERISTICS:
  (A) LENGTH: 25 base pairs
  (B) TYPE: nucleic acid
  (C) STRANDEDNESS: single
  (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
  (A) ORGANISM: Equus caballus (v i i) IMMEDIATE SOURCE:
  (B) CLONE: 670

(x i) SEQUENCE DESCRIPTION: SEQ ID NO:21:

TGTTCTGGGA AAGACCACAT TATTT   25

(2) INFORMATION FOR SEQ ID NO:22:

(i) SEQUENCE CHARACTERISTICS:
  (A) LENGTH: 30 base pairs
  (B) TYPE: nucleic acid
  (C) STRANDEDNESS: single
  (D) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Equus caballus ( v i i ) IMMEDIATE SOURCE:
                ( B ) CLONE: 1241

( x i ) SEQUENCE DESCRIPTION: SEQ ID NO:22:

GAACAAAATA ATGTGGTCTT TCCCAGAACA                                                        30

( 2 ) INFORMATION FOR SEQ ID NO:23:

( i ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Equus caballus ( v i i ) IMMEDIATE SOURCE:
                ( B ) CLONE: 1242

( x i ) SEQUENCE DESCRIPTION: SEQ ID NO:23:

GAACTAAATA ATGTGGTCTT TCCCAGAACA                                                        30

( 2 ) INFORMATION FOR SEQ ID NO:24:

( i ) SEQUENCE CHARACTERISTICS:
                ( A ) LENGTH: 25 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Equus caballus ( v i i ) IMMEDIATE SOURCE:
                ( B ) CLONE: 431

( x i ) SEQUENCE DESCRIPTION: SEQ ID NO:24:

AGCCTCAGAC CGCGTGGTGC CTGGT                                                             25

METHOD FOR IMMOBILIZING NUCLEIC ACID MOLECULES

CROSS-REFERENCE TO RELATED APPLICATIONS

This application is a continuation-in-part of U.S. patent application Ser. No. 08/162,397, filed Dec. 6, 1993, now abandoned, herein incorporated by reference.

FIELD OF THE INVENTION

The invention relates to a simple method for immobilizing synthetic nucleic acid molecules onto a solid support. The invention further concerns the use of such immobilized molecules in nucleic acid hybridization assays, nucleic acid sequencing, and in the analysis of genomic polymorphisms.

BACKGROUND OF THE INVENTION

The analysis of the structure, organization and sequence of nucleic acid molecules is of profound importance in the prediction, diagnosis and treatment of human and animal disease, in forensics, in epidemiology and public health, and in the elucidation of the factors that control gene expression and development. Methods for immobilizing nucleic acids are often important in these types of analyses. Three areas of particular importance involve hybridization assays, nucleic acid sequencing, and the analysis of genomic polymorphisms.

I. Nucleic Acid Hybridization

The capacity of a nucleic acid "probe" molecule to hybridize (i.e. base pair) to a complementary nucleic acid "target" molecule forms the cornerstone for a wide array of diagnostic and therapeutic procedures.

Hybridization assays are extensively used in molecular biology and medicine. Methods of performing such hybridization reactions are disclosed by, for example, Sambrook, J. et al. (In: *Molecular Cloning: A Laboratory Manual*, Cold Spring Harbor Laboratory Press, Cold Spring Harbor, N.Y. (1989)), Haymes, B. D., et al. (In: *Nucleic Acid Hybridization, A Practical Approach*, IRL Press, Washington, D.C. (1985)) and Keller, G. H. and Manak, M. M. (In: *DNA Probes, Second Edition*, Stockton Press, New York, N.Y. (1993)) which references are incorporated herein by reference.

Many hybridization assays require the immobilization of one component. Nagata et al. described a method for quantifying DNA which involved binding unknown amounts of cloned DNA to microtiter wells in the presence of 0.1M $MgCl_2$ (Nagata et al., *FEBS Letters* 183: 379–382, 1985). A complementary biotinylated probe was then hybridized to the DNA in each well and the bound probe measured colorimetrically. Dahlen, P. et al. have discussed sandwich hybridization in microtiter wells using cloned capture DNA adsorbed to the wells (Dahlen, P. et al., *Mol. Cell. Probes* 1: 159–168, 1987). An assay for the detection of HIV-1 DNA using PCR amplification and capture hybridization in microtiter wells has also been discussed (Keller, G. H. et al., *J. Clin. Microbiol.* 29: 638–641, 1991 ). The NaCl-mediated binding of oligomers to polystyrene wells has been discussed by Cros et al. (French patent no. 2,663,040) and very recently by Nikiforov et al. (*PCR Methods Applic.* 3: 285–291, 1994). The cationic detergent-mediated binding of oligomers to polystyrene wells has very recently been described by Nikiforov et al., *Nucleic Acids Res.* 22: 4167–4175.

II. Analysis Of Single Nucleotide DNA Polymorphisms

Many genetic diseases and traits (i.e. hemophilia, sickle-cell anemia, cystic fibrosis, etc.) reflect the consequences of mutations that have arisen in the genomes of some members of a species through mutation or evolution (Gusella, J. F., *Ann. Rev. Biochem.* 55:831–854 (1986)). In some cases, such polymorphisms are linked to a genetic locus responsible for the disease or trait; in other cases, the polymorphisms are the determinative characteristic of the condition.

Such single nucleotide polymorphisms differ significantly from the variable nucleotide type polymorphisms ("VNTRs"), that arise from spontaneous tandem duplications of di- or tri-nucleotide repeated motifs of nucleotides (Weber, J. L., U.S. Pat. No. 5,075,217; Armour, J. A. L. et al., *FEBS Lett.* 307:113–115 (1992); Jones, L. et al., *Eur. J. Haematol.* 39:144–147 (1987); Horn, G. T. et al., PCT Application WO91/14003; Jeffreys, A. J., U.S. Pat. No. 5,175,082); Jeffreys. A. J. et al., *Amer. J. Hum. Genet.* 39:11–24 (1986); Jeffreys. A. J. et al., *Nature* 916:76–79 (1985); Gray, I. C. et al., *Proc. R. Acad. Soc. Lond.* 243:241–253 (1991); Moore, S. S. et al., *Genomics* 10:654–660 (1991); Jeffreys, A. J. et al., *Anim. Genet.* 18:1–15 (1987); Hillel, J. et al., *Anim. Genet.* 20:145–155 (1989); Hillel, J. et al., *Genet.* 124:783–789 (1990)), and from the restriction fragment length polymorphisms ("RFLPs") that comprise variations which alter the lengths of the fragments that are generated by restriction endonuclease cleavage (Glassberg, J., UK patent application 2135774; Skolnick, M. H. et al., *Cytogen. Cell Genet.* 32:58–67 (1982); Botstein, D. et al., *Ann. J. Hum. Genet.* 32:314–331 (1980); Fischer, S. G. et al. (PCT Application WO90/13668); Uhlen, M., PCT Application WO90/11369)).

Because single nucleotide polymorphisms constitute sites of variation flanked by regions of invariant sequence, their analysis requires no more than the determination of the identity of the single nucleotide present at the site of variation; it is unnecessary to determine a complete gene sequence for each patient. Several methods have been developed to facilitate the analysis of such single nucleotide polymorphisms.

Mundy, C. R. (U.S. Pat. No. 4,656,127), for example, discusses a method for determining the identity of the nucleotide present at a particular polymorphic site that employs a specialized exonuclease-resistant nucleotide derivative. A primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. The Mundy method has the advantage that it does not require the determination of large amounts of extraneous sequence data. It has the disadvantages of destroying the amplified target sequences, and unmodified primer and of being extremely sensitive to the rate of polymerase incorporation of the specific exonuclease-resistant nucleotide being used.

Cohen, D. et al. (French Patent 2,650,840; PCT Appln. No. WO91/02087) discuss a solution-based method for determining the identity of the nucleotide of a polymorphic site. As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase. It is thus easier to perform, and more accurate than the method discussed by Cohen.

An alternative approach, the "Oligonucleotide Ligation Assay" ("OLA") (Landegren, U. et al., *Science* 241:1077–1080 (1988)) has also been described as capable of detecting single nucleotide polymorphisms. The OLA protocol uses two oligonucleotides which are designed to be capable of hybridizing to abutting sequences of a single strand of a target. One of the oligonucleotides is biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al., *Proc. Natl. Acad. Sci. (U.S.A.)* 87:8923–8927 (1990). In this method, PCR is used to achieve the exponential amplification of target DNA, which is then detected using OLA. In addition to requiring multiple, and separate, processing steps, one problem associated with such combinations is that they inherit all of the problems associated with PCR and OLA.

Recently, several primer-guided nucleotide incorporation procedures for assaying polymorphic sites in DNA have been described (Komher, J. S. et al., *Nucl. Acids. Res.* 17:7779–7784 (1989); Sokolov, B. P., *Nucl. Acids Res.* 18:3671 (1990); Syvänen, A. -C., et al., *Genomics* 8:684–692 (1990); Kuppuswamy, M. N. et al., *Proc. Natl. Acad. Sci. (U.S.A.)* 88:1143–1147 (1991); Prezant, T. R. et al., *Hum. Mutat.* 1:159–164 (1992); Ugozzoli, L. et al., *GATA* 9:107–112 (1992); Nyrén, P. et al., *Anal. Biochem.* 208:171–175 (1993)). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvänen, A. C., et al., *Amer. J. Hum. Genet.* 52:46–59 (1993)). Such a range of locus-specific signals could be more complex to interpret, especially for heterozygotes, compared to the simple, ternary (2:0, 1:1, or 0:2) class of signals produced by the GBA™ method. In addition, for some loci, incorporation of an incorrect deoxynucleotide can occur even in the presence of the correct dideoxynucleotide (Komher, J. S. et al., *Nucl. Acids. Res.* 17:7779–7784 (1989)). Such deoxynucleotide misincorporation events may be due to the Km of the DNA polymerase for the mispaired deoxy-substrate being comparable, in some sequence contexts, to the relatively poor Km of even a correctly base paired dideoxy-substrate (Kornberg, A., et al., In: DNA Replication, Second Edition (1992), W. H. Freeman and Company, New York; Tabor, S. et al., *Proc. Natl. Acad. Sci. (U.S.A.)* 86:4076–4080 (1989)). This effect would contribute to the background noise in the polymorphic site interrogation.

III. Oligonucleotide Immobilization On Plastic And Glass

Several of the above-described methods involve procedures in which one or more of the nucleic acid reactants are immobilized to a solid support. Currently, 96-well polystyrene plates are widely used in solid-phase immunoassays, and several PCR product detection methods that use plates as a solid support have been described. The most specific of these methods require the immobilization of a suitable oligonucleotide probe into the microtiter wells followed by the capture of the PCR product by hybridization and colorimetric detection of a suitable hapten. It would be desirable to have an improved immobilization method that could be used to bind oligonucleotides to polystyrene such that their capacity to be used for hybridization, sequencing, or polymorphic analysis would be retained, and which would be rapid, convenient to use and inexpensive. The present invention provides such an improved method.

The means by which macromolecules bind non-covalently to polystyrene and glass surfaces is not well understood. Nevertheless, these adsorption phenomena have proven to be important in the development and manufacturing of immunoassays and other types of diagnostic tests where one component needs to be immobilized.

Polystyrene is a very hydrophobic material because it normally contains no hydrophilic groups. Microtiter plate manufacturers have developed methods of introducing such groups (hydroxyl, carboxyl, carbonyl and others) onto the surface of microwells to increase the hydrophilic nature of the surface. Theoretically, this allows macromolecules to bind through a combination of hydrophobic and hydrophilic interactions (Baler et al., *Science* 162:1360–1368 (1968); Baler et al., *J. Biomed. Mater. Res.* 18:335–355 (1984); Good et al., in L. H. Lee (ed.) *Fundamentals of Adhesion*, Plenum, N.Y., chapter 4 (1989)) (FIG. 1). In practice, some proteins do bind more efficiently to the treated hydrophilic polystyrene than to the untreated material. Covalent binding to polystyrene, especially microtiter wells, has proven to be difficult, so passive adsorption remains the most commonly used method of binding macromolecules to such wells. The term "polystyrene" may also be used to describe styrene-containing copolymers such as: styrene/divinyl benzene, styrene/butadiene, styrene/vinyl benzyl chloride and others.

While polystyrene is an organic hydrophobic substrate, glass provides an inorganic hydrophobic surface with hydrophilic islands. The most common glass format in immunoassays is the microscope slide. Laboratory-grade glasses are predominantly composed of $SiO_2$, but they also may contain $B_2O_3$, $Na_2O$, $Al_2O_3$ as well as other oxides (FIG. 2).

SUMMARY OF THE INVENTION

The present invention provides an improved immobilization method that permits the rapid, and inexpensive immobilization of nucleic acid molecules to a solid support. The invention is extremely simple, allowing immobilization of oligonucleotides by incubation with a salt or a cationic detergent. The immobilized molecules can be used for hybridization, sequencing, or polymorphic analysis.

In detail, the invention provides a method for immobilizing a nucleic acid molecule to a polystyrene or glass support, the method comprising the steps:

(A) incubating the nucleic acid molecule in the presence of the solid support; the incubation being in the presence of a reagent selected from the group consisting of the inorganic salt sodium chloride (NaCl), the organic salt tetramethylammonium chloride (($CH_3$)$_4$NCl) (both preferably provided at a concentration of at least about 50 mM) and a cationic detergent (preferably provided at a concentration of 0.03 to 100 mM)]; and (B) subsequently the washing support with an aqueous solution of a non-ionic detergent.

The invention particularly concerns the embodiments of the above method wherein, in step A, the cationic detergent is a water-soluble carbodiimide (preferably EDC, provided at a concentration of from about 30 mM to about 100 mM) or wherein the cationic detergent is selected from the group consisting of octyldimethylamine (provided at a concentration of from about 50 mM to about 150 mM) and cetyl triethyl ammonium bromide (provided at a concentration of from about 0.03 mM to about 0.25 mM).

The invention further concerns the embodiments of the above methods wherein, in step B, the non-ionic detergent is Tween, preferably provided in a solution that additionally contains buffered saline.

The invention is additionally directed to the embodiments of the above methods wherein the nucleic acid molecule has a length of at least 12 nucleotide residues, up to 100 residues and a 3' and a 5'-terminus, and wherein such molecule is immobilized to the support by non-covalent interactions at the oligonucleotide's 3'-terminus, an internal region or, at its 5'-terminus.

The invention further concerns the embodiments of the above methods wherein the oligonucleotides are applied to the support in a specific pattern or grid by microdeposition methods such as inkjet printing. Another embodiment involves the immobilization of oligonucleotides to polystyrene pins, arranged in an array matching a standard 96-well plate.

DESCRIPTION OF THE PREFERRED EMBODIMENTS

Figure 1:
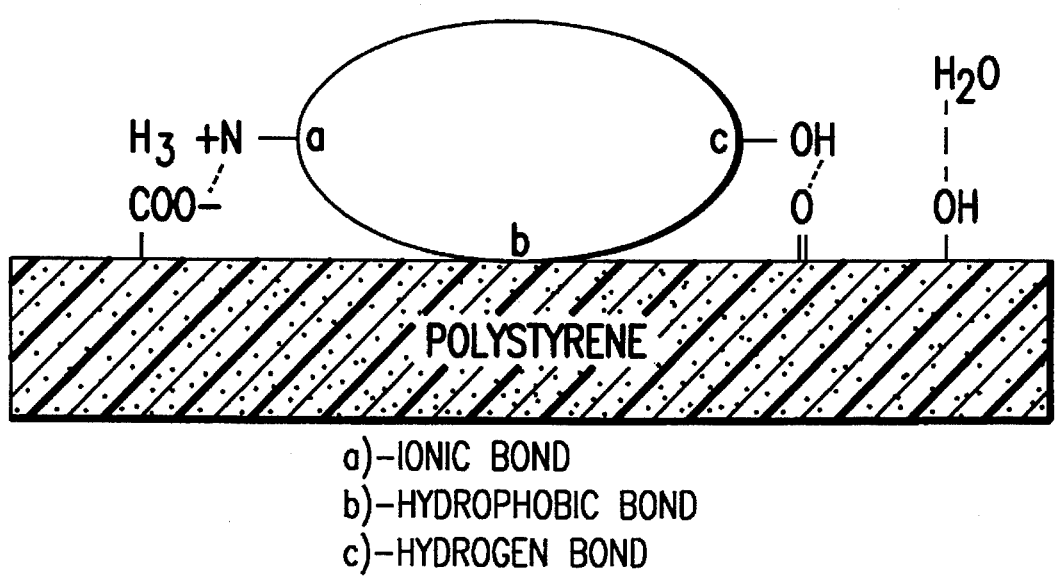
FIG. 1 illustrates the binding of a generic macromolecule to a hydrophilic polystyrene surface.
Figure 2:
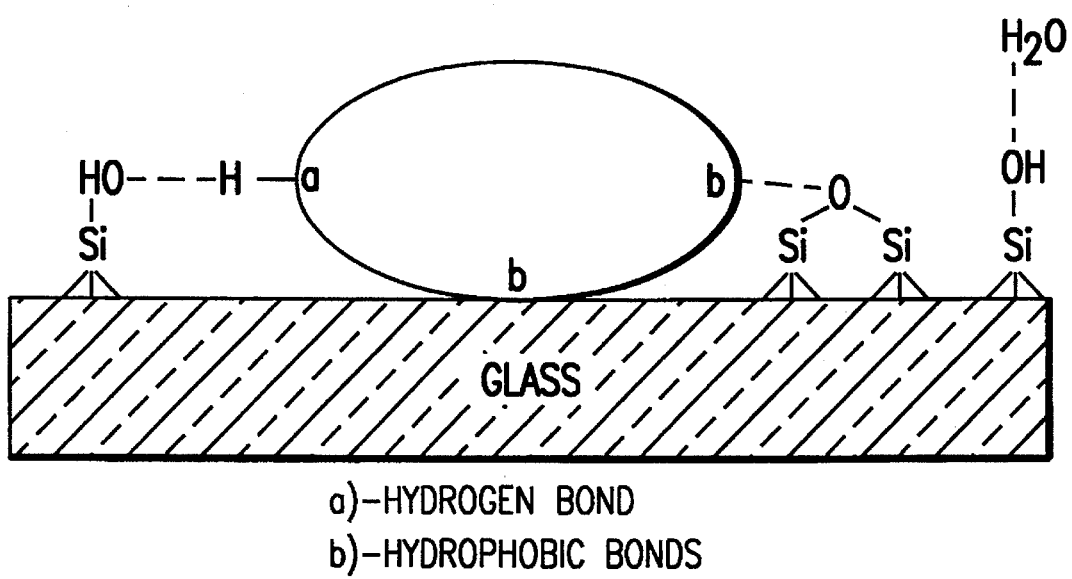
FIG. 2 illustrates the binding of a generic macromolecule to a typical glass surface.

I. The Immobilization of Nucleic Acid Molecules

The present invention concerns a method for immobilizing a synthetic nucleic acid molecule onto a solid support. Recently, several methods have been proposed as suitable for immobilizing an oligonucleotide to a solid support. Holmstrom, K. et al., for example, exploit the affinity of biotin for avidin and streptavidin, and immobilize biotinylated nucleic acid molecules to avidin/streptavidin coated supports (Holmstrom, K. et al., *Anal. Biochem.* 209:278–283 (1993)). Another recent method requires the precoating of the polystyrene or glass solid phases with poly-L-Lys or poly L-Lys, Phe, followed by the covalent attachment of either amino- or sulfhydryl-modified oligonucleotides using bifunctional crosslinking reagents. Both methods have the disadvantage of requiring the use of modified oligonucleotides as well as a pretreatment of the solid phase (Running. J. A. et .al., *BioTechniques* 8:276–277 (1990); Newton, C. R. et al. *Nucl. Acids Res.* 21:1155–1162 (1993)).

Kawai, S. et..al. describe an alternative method in which short oligonucleotide probes were ligated together to form multimers and these were ligated into a phagemid vector (Kawai, S. et al., *Anal. Biochem.* 209:63–69 (1993)). The oligonucleotides were immobilized onto polystyrene plates and fixed by UV irradiation at 254 nm. A method for the direct covalent attachment of short, 5'-phosphorylated primers to chemically modified polystyrene plates ("Covalink" plates, Nunc) has also been proposed by Rasmussen, S. R. et al., (*Anal. Biochem.* 196:138–142 (1991)). The covalent bond between the modified oligonucleotide and the solid phase surface is introduced by condensation with a water-soluble carbodiimide. This method is claimed to assure a predominantly 5'-attachment of the oligonucleotides via their 5'-phosphates; however, it requires the use of specially prepared, expensive plates.

The methods of the present invention depart from such methods, in not requiring either the presence of specially modified nucleotides in the molecule to be immobilized, or the use of expensively modified supports. Any nucleic acid molecule (RNA or DNA) may be immobilized to such supports using the methods of the present invention. The nucleic acid molecules may ideally be 12–100 nucleotides long, and may be immobilized to the support at either their 3'-terminus, their 5'-terminus, or at an internal (i.e. non-terminal) region.

A nucleic acid molecule is said to be "immobilized" to a solid support if it is either adsorbed to the support, or bonded thereto, with sufficient strength that it cannot be removed from the support by washing with water or an aqueous buffer. Knowledge of the precise chemical mechanism through which such immobilization occurs is not needed for use of the present invention.

Although any of a variety of glass or plastic solid supports can be used in accordance with the methods of the present invention, polystyrene is the preferred support. The support can be fashioned as a bead, dipstick, test tube, etc. The conventional 96-well polystyrene microtiter dishes used in diagnostic laboratories and in tissue culture are, however, an especially preferred support. Any of a number of commercially available polystyrene plates can be used directly for the immobilization, provided that they have hydrophilic groups on the plastic surface. Examples of suitable plates include the Immulon 4 plates (Dynatech) and the Maxisorp plates (Nunc). Methods for synthesizing polystyrene are known in the art; such methods are disclosed in, for example, treatises on plastics and polymers such as Byrdson, J. A., *Plastics Materials*, Fifth Edition, Butterworth Heinemann, London (1991), herein incorporated by reference.

Remarkably, in the method of the present invention, unmodified oligonucleotides can be efficiently immobilized onto the surface of a hydrophilic polystyrene plate simply by incubation in the presence of one of two different groups of reagents that can be characterized as either salts or cationic detergents. A hydrophilic polystyrene plate is defined as one treated by the manufacturer or user to increase the number of hydrophilic groups (i.e., —OH, —C=O, —COOH) on the surface of the plastic. No immobilization takes place in the absence of a salt or cationic detergent, i.e., when the oligonucleotide is present in a salt-free or cationic detergent-free water solution.

The first group consists of chemicals like NaCl and $(CH_3)_4NCl$, which work best when used at relatively high concentrations, generally higher than 50 mM, and best at 250 to 500 mM. Even concentrations as high as 1M can be used without any noticeable adverse effect on the immobilization. The second group of immobilization reagents consists of chemicals that are characterized by the presence of two structural features: a positively charged "head" and a relatively hydrophobic "tail". These are the typical features of cationic detergents. Representatives of this group include the cationic detergent cetyltrimethyl ammonium bromide (CTAB), octyldimethylamine hydrochloride, and 1-ethyl-3-(3'-dimethylaminopropyl)-1,3-carbodiimide hydrochloride (EDC). These compounds can be used for oligonucleotide immobilization at very low concentrations, as low as 0.03 mM for CTAB, but they inhibit the immobilization when used at higher concentrations. The inhibitory concentration differs between the reagents of this group. For CTAB, it is as low as 0.5 mM, whereas for EDC it is about 500 mM. It should be noted that the critical micelle concentration, cmc, for CTAB is about 1 mM. Thus, it seems that once micelles are formed, the immobilization is inhibited. Compounds of a similar structure, but with a negatively charged "head" (or nonionic detergents) are completely inactive as oligonucleotide immobilization reagents. A typical representative here is the anionic detergent SDS (sodium dodecyl sulfate), which was found inactive over a very large range of different concentrations (0.025 mM to 100 mM).

It is reasonable to assume that the two groups of reagents mentioned above promote the immobilization of oligonucleotides to polystyrene plates by different mechanisms. In the presence of NaCl and other salts, the hydrophobic interactions between the oligonucleotide molecule and hydrophobic regions at the polystyrene surface are enhanced to a degree that allows the immobilization of the former. The presence of a salt (increased ionic strength of the solution) decreases electrostatic repulsion between the phosphates of the oligonucleotide backbone and negatively charged groups on the polystyrene surface. This reduction should enhance the hydrophobic binding of the oligonucleotide molecules.

The mechanism of binding in the presence of cationic detergents is probably quite different. Here, initially there is association in solution between the negatively charged oligonucleotides and the positively charged detergent-like molecules. The number of detergent molecules that associate with each oligonucleotide molecule will be dependent on the oligonucleotide length, but should be significantly higher than one in the case of a 25 mer oligonucleotide. This association of oligonucleotides with detergents containing a hydrophobic tail will render the oligonucleotide significantly hydrophobic and will lead to its immobilization to the plate surface by hydrophobic interactions. In effect these molecules appear to act as a linker between the hydrophobic areas of the plate and the charged phosphate backbone of the oligonucleotide.

If the concentration of the detergent molecules is higher than their cmc, micelles will be formed. Although oligonucleotides might still interact with the detergent molecules, they will be included in the micelles, and since the micelles have a hydrophobic core that is completely surrounded by a polar surface, no hydrophobic interactions with the surface will occur and therefore oligonucleotide immobilization will be diminished or prevented. The different inhibitory concentrations observed for the different reagents reflect the widely different concentrations at which these reagents will form micelles. For CTAB, a very good detergent, the cmc is very low, whereas EDC and octyldimethylamine hydrochloride, which are very poor detergents, form micelles and inhibit the immobilization only at relatively high concentrations.

An example of a suitable salt is sodium chloride (NaCl). When it is desired to employ NaCl, concentrations of from about 50 mM to about 250 mM may be used; a concentration of at least 50 mM is desirable in order to achieve optimal immobilization (hydrophobic interactions are stronger at higher salt concentrations). Examples of suitable cationic detergents are 1-ethyl-3-(3'-dimethylaminopropyl)carbodiimide hydrochloride, pH about 6.8 ("EDC") and tertiary alkyl amines such as cetyl trimethyl ammonium bromide and octyl dimethyl amine HCl. EDC may be employed at concentrations (in water) of from about 30 mM to about 100 mM. Varga, J. M. et al. have shown that various small biomolecules can be immobilized to polystyrene plates by incubation with 1-ethyl-3-(3'-dimethylaminopropyl)carbodiimide hydrochloride ("EDC") (Varga, J. M. et al., *FASEB* 4:2671–2677 (1990)). However, no examples of oligonucleotide immobilization were provided, and it is generally believed that short, single-stranded oligonucleotide molecules are immobilized only very inefficiently to polystyrene supports. Lacy et al. (*J. Immunl. Methods* 116:87–98 (1989)) have reported the binding of calf thymus DNA to polystyrene in the presence of high salt and high pH, but presented evidence that a synthetic oligonucleotide did not bind.

A preferred tertiary alkyl amine is octyldimethylamine, which may be used at concentrations of from about 50 mM to about 150 mM. Octyldimethylamine has a structure that is very similar to that of EDC, however, octyldimethylamine does not contain the reactive diimide functional group of EDC. This demonstrates that EDC does not mediate covalent binding to polystyrene, but indeed acts as a detergent (hydrophilic/hydrophobic molecule). Tetramethylammonium chloride may also be used, preferably at a concentration of from about 50 mM to about 250 mM.

The immobilization is achieved by incubation, preferably at room temperature for 3 to 24 hours. After such incubation, the plates are washed, preferably with a solution of 10 mM Tris HCl, pH 7.5, containing 150 mM NaCl and 0.05% vol. Tween 20 (TNTw). The latter ingredient serves the important role of blocking all free oligonucleotide binding sites still present on the polystyrene surface, so that no non-specific binding of oligonucleotides can take place during any subsequent hybridization step. The above procedure could immobilize at least 500 fmoles of oligonucleotide per well (corresponding to a surface area of about 1 $cm^2$). The oligonucleotides are immobilized to the surface of the plate with sufficient stability and can only be removed by prolonged incubations with 0.5M NaOH solutions at elevated temperatures. No oligonucleotide is removed by washing the plate with water, TNTw (Tween 20), PBS, 1.5M NaCl, or other similar aqueous buffers.

Such procedures and reagents can effectively immobilize unmodified oligonucleotides as well as modified (for example, biotinylated) oligonucleotides. The immobilization mediated by these reagents is not believed to reflect covalent bonding between the nucleic acid, and reactive groups of the support. Without limitation to the scope of the present invention, the immobilization is believed to be non-covalent, and to reflect a combination of hydrophobic, ionic and hydrogen bonding interactions to the polystyrene surface of the support.

Whatever the exact mechanism of immobilization, the reagents of the present invention are capable of mediating an attachment of oligonucleotides to a solid support that has sufficient stability to resist washing, and to sustain a one hour treatment with 0.1N NaOH. Moreover, the immobilized oligonucleotides can efficiently participate in hybridization reactions. Although shorter oligonucleotides can also be immobilized, a length of at least 12 bases was found to be required in order to be able to efficiently hybridize to complementary DNA molecules. This observation suggests that the process of immobilization of the oligonucleotide to the solid support renders short portions of the immobilized molecules inaccessible to hybridization.

In accordance with the present invention, the immobilization reagent is incubated in the presence of the oligonucleotide that is to be immobilized and the solid support. Suitable incubations may vary in duration, and preferably will be maintained overnight. Incubation may be performed at room temperature.

The nucleic acid molecules that are to be immobilized on the solid support can be synthesized chemically, or can be recovered from a natural source. Alternatively, such molecules can be produced via an in vitro amplification protocol, such as PCR. Short oligonucleotides are more preferably obtained via chemical synthesis.

II. The Use of Immobilized Oligonucleotides in Genetic Analysis

The methods of the present invention are particularly useful in producing immobilized oligonucleotides for solid phase hybridization, for solid phase dideoxy sequencing studies, and for analysis of DNA polymorphisms.

A. Hybridization Detection Of PCR Products

Thus, for example, they may be used to detect specific PCR products by hybridization where the capture probe is immobilized on the solid phase (Ranki et al., Gene 21: 77–85, 1983; Keller et al., J. Clin. Microbiol. 29: 638–641, 1991; Urdea et al., Gene 61: 253–264, 1987). A preferred method would be to prepare a single-stranded PCR product before hybridization. A sample, suspected to contain the target molecule, or an amplification product thereof, would then be added to the well and permitted to hybridize to the bound oligonucleotide.

The methods of the present invention do not require that the target nucleic acid contain only one of its natural two strands. Thus, the methods of the present invention may be practiced on either double-stranded DNA, or on single-stranded DNA obtained by, for example, alkali treatment of native DNA. The presence of the unused (non-template) strand does not affect the reaction.

Where desired, however, any of a variety of methods can be used to eliminate one of the two natural stands of the target DNA molecule from the reaction. Single-stranded DNA molecules may be produced using the single-stranded DNA bacteriophage M13 (Messing, J. et al., *Meth. Enzymol.* 101:20 (1983); see also, Sambrook, J., et al. (In: *Molecular Cloning: A Laboratory Manual*, Cold Spring Harbor Laboratory Press, Cold Spring Harbor, N.Y. (1989)).

Several alternative methods can be used to generate single-stranded DNA molecules. Gyllensten, U. et al., (*Proc. Natl. Acad. Sci. (U.S.A.)* 85:7652–7656 (1988) and Mihovilovic, M. et al., (*BioTechniques* 7:14 (1989)) describe a method, termed "asymmetric PCR," in which the standard "PCR" method is conducted using primers that are present in different molar concentrations. Higuchi, R. G. et al. (*Nucleic Acids Res.* 17:5865 (1985)) exemplifies an additional method for generating single-stranded amplification products. The method entails phosphorylating the 5'-terminus of one strand of a double-stranded amplification product, and then permitting a 5' Æ 3' exonuclease (such as exonuclease) to preferentially degrade the phosphorylated strand.

Other methods have also exploited the nuclease resistant properties of phosphorothioate derivatives in order to generate single-stranded DNA molecules (Benkovic et al., U.S. Pat. No. 4,521,509; Jun. 4, 1985); Sayers, J. R. et al. (*Nucl. Acids Res.* 16:791–802 (1988); Eckstein, F. et al., *Biochemistry* 15:1685–1691 (1976); Ott, J. et al., *Biochemistry* 26:8237–8241 (1987)).

Most preferably, such single-stranded molecules will be produced using the methods described by Nikiforov, T. (commonly assigned U.S. patent application Ser. No. 08/155,746, herein incorporated by reference). In brief, these methods employ nuclease resistant nucleotide derivatives, and incorporate such derivatives, by chemical synthesis or enzymatic means, into primer molecules, or their extension products, in place of naturally occurring nucleotides.

Suitable nucleotide derivatives include derivatives in which one or two of the non-bridging oxygens of the phosphate moiety of a nucleotide has been replaced with a sulfur-containing group (especially a phosphorothioate), an alkyl group (especially a methyl or ethyl alkyl group), a nitrogen-containing group (especially an amine), and/or a selenium-containing group, etc. Phosphorothioate deoxyribonucleotide or ribonucleotide derivatives are the most preferred nucleotide derivatives. Methods of producing and using such phosphorothioate derivatives are disclosed by Nikiforov, T. (U.S. patent application Ser. No. 08/155,746).

B. Solid Phase DNA Sequencing

The methods of the present invention may also be used in the practice of solid-phase sequencing as described by Khrapko, K. R. et al. (DNA Seq.: 1, 375–388, 1991) and Drmanac, R. and Crkvenjakov, R.,*Int. J. Genome RES.*: 1, 1–1, 1992), both herein incorporated by reference.

C. GBA™ Genetic Bit Analysis

The methods of the present invention may also be used to immobilize the oligonucleotides that are used in the GBA™ Genetic Bit Analysis (Goelet, P. et al., PCT Appln. No. 92/15712). Oligonucleotides having a defined sequence complementary to a region that lies immediately proximal or distal to the variable nucleotide of a polymorphism would thus be provided to a polystyrene microtiter well, and incubated with a salt, in accordance with the above-described methods.

The immobilized primer is then incubated in the presence of a DNA molecule (preferably a genomic DNA molecule) having a single nucleotide polymorphism whose immediately 3'-distal sequence is complementary to that of the immobilized primer. Preferably, such incubation occurs in the complete absence of any dNTP (i.e. dATP, dCTP, dGTP, or dTTP), but only in the presence of one or more chain terminating nucleotide triphosphate derivatives (such as a dideoxy derivative), and under conditions sufficient to permit the incorporation of such a derivative on to the 3'-terminus of the primer. As will be appreciated, where the polymorphic site is such that only two or three alleles exist (such that only two or three species of ddNTPs, respectively, could be incorporated into the primer extension product), the presence of unusable nucleotide triphosphate(s) in the reaction is immaterial. In consequence of the incubation, and the use of only chain terminating nucleotide derivatives, a single dideoxynucleotide is added to the 3'-terminus of the primer. The identity of that added nucleotide is determined by, and is complementary to, the nucleotide of the polymorphic site of the polymorphism.

In this embodiment, the nucleotide of the polymorphic site is thus determined by assaying which of the set of labeled nucleotides has been incorporated onto the 3'-terminus of the bound oligonucleotide by a primer-dependent polymerase. Most preferably, where multiple dideoxynucleotide derivatives are simultaneously employed, different labels will be used to permit the differential determination of the identity of the incorporated dideoxynucleotide derivative.

D. Ligase-Mediated GBA™

The methods and reagents of the present invention can also be used in concert with a polymerase/ligase mediated polymorphic interrogation assay. This assay, termed ligase-mediated GBA™ genetic bit analysis, is a more specific version of the GBA™ genetic bit analysis assay. The additional specificity arises from the addition of a second hybridization step and a ligation step.

In this assay, two oligonucleotides are employed. The first oligonucleotide is a primer that is complementary to the immediately 3'-distal invariant sequence of the polymorphism. The 3'-end of the oligonucleotide is attached to the plate. A second linker oligonucleotide is complementary to the 5'-proximal sequence of the polymorphism being analyzed, but is incapable of hybridizing to the first oligonucleotide. This oligonucleotide is phosphorylated at its 3' and 5' ends.

These oligonucleotides are incubated in the presence of DNA containing the single nucleotide polymorphism that is to be analyzed, and at least one 2'-deoxynucleotide 5'-triphosphate. The incubation reaction further includes a DNA polymerase and a DNA ligase. The tethered and soluble oligonucleotides are thus capable of hybridizing to the same strand of the target molecule under analysis. The sequence considerations cause the two oligonucleotides to hybridize to the proximal and distal sequences of the single nucleotide polymorphism (SNP) that flank the variable nucleotide of the polymorphism, and to be separated by a single nucleotide at the precise position of the variability.

The presence of a polymerase and the 2'-deoxynucleotide 5'-triphosphate complementary to the nucleotide present in the variable site of the polymorphism permits the extended primer to be ligated to the bound oligonucleotide, thereby immobilizing the primer. The identity of the polymorphic site that was opposite the single nucleotide can then be determined by any of several means. In a preferred embodiment, the 2'-deoxynucleotide 5'-triphosphate of the reaction is labeled, and its detection thus reveals the identity of the complementary nucleotide of the polymorphic site. Several different 2'-deoxynucleotide 5'-triphosphates may be present, each differentially labeled. Alternatively, separate reactions can be conducted, each with a different 2'-deoxynucleotide 5'-triphosphate. In an alternative sub-embodiment, the 2'-deoxynucleotide 5'-triphosphates are unlabeled, and the soluble oligonucleotide is labeled. In this embodiment, the primer that is extended is immobilized on the polystyrene. Separate reactions are conducted, each using a different unlabeled 2'-deoxynucleotide 5'-triphosphate.

Having now generally described the invention, the same will be more readily understood through reference to the following examples of the isolation and analysis of equine polymorphisms which are provided by way of illustration, and are not intended to be limiting of the present invention.

EXAMPLE 1

Demonstration of Different Binding Mechanisms for Salts and Cationic Detergents

An indication that salts and cationic detergents mediate different mechanisms of immobilization was provided by the following experiment in which three different oligonucleotide molecules and one biotinylated polyphosphate were immobilized to polystyrene plates using three different reagents: EDC at 20 mM, CTAB at 0.03 mM and NaCl at 500 mM. The biotinylated oligonucleotides used were #1129, biotin-$T_5$, and biotin-$T_{25}$. The #1129 oligonucleotide has the following sequence:

SEQ ID NO:1 5'-B-ACCAGGCACCACGCGGTCT-GAGGCT

SEQ ID NO:2 5-B-TTTTTTTTTTTTTTTTTTTTTTTTT

The biotinylated polyphosphate had the structure biotin-$(C_3)_{25}$, where $C_3$ is $CH_2CH_2CH_2OPO_3$. This polyphosphate has the phosphodiester bonds of a regular oligonucleotide, but lacks the deoxyribose residues and the heterocyclic bases. The results from this experiment are summarized in Table 1. The results are expressed in $mOD_{450}$/min.

TABLE 1

| Effect of Salts and detergents on Oligonucleotide Binding | | | |
|---|---|---|---|
| Oligo | EDC | CTAB | NaCl |
| #1129 | 350 | 420 | 450 |
| biotin-$T_5$ | 390 | 450 | 430 |
| biotin-$T_{25}$ | 460 | 480 | 450 |
| biotin-$(C_3)_{25}$ | 620 | 580 | 50 |

Table 1 shows that while all three reagents tested were effective in the immobilization of the three biotinylated oligonucleotides, the polyphosphate biotin-$(C_3)_{25}$ could not be efficiently immobilized to the polystyrene plate by 500 mM NaCl. The inefficiency of NaCl in the immobilization of biotin-$(C_3)_{25}$ could be explained by the intrinsically lower hydrophobicity of this molecule compared to a typical oligonucleotide. This reduced hydrophobicity is due to the lack of the deoxyribose residues and the heterocyclic bases. Thus, the presence of NaCl is not sufficient to promote hydrophobic binding of this molecule to the plate surface. On the other hand, biotin-$(C_3)_{25}$ does form complexes in solution with EDC or CTAB by electrostatic interactions. These complexes significantly increase the hydrophobicity of this polyphosphate and promote its immobilization to the polystyrene.

EXAMPLE 2

Concentration Dependence of Binding with Salts or Cationic Detergents

Immobilization of oligonucleotides to polystyrene plates. The use of CTAB and $(CH_3)_4NCl$ as examples of two reagents that work by different mechanisms. The oligonucleotide #1112 was immobilized onto Immulon 4 plates (Dynatech, Va.). The nucleotide sequence of #1112 is:

SEQ ID NO:3 5'-AGTATAATAATCACAGTATGTTAGC

The immobilization was carried out using 10 pmole of oligonucleotide in 50 µl immobilization solution per well of the microtiter plate. The immobilization reagents were used at the following concentrations:

CTAB: 0.5, 0.25, 0.12, 0.06, and 0.03 mM $(CH_3)_4NCl$: 300, 150, 30, 0.3, and 0.03 mM As negative controls, the oligonucleotides were added to some of the wells without any immobilization reagents (i.e., as aqueous solutions).

To assess the immobilization of these oligonucleotides, following an overnight incubation the plates were washed three times with TNTw and a biotinylated oligonucleotide (#1676) complementary to the oligonucleotide #1112 was added at different concentrations (31, 62, 125, and 250 fmole per well). The biotinylated oligonucleotide #1676 had the following sequence:

SEQ ID NO:4 5'B-CCACGGCTAACATACTGTGAT-TATTATACTTAGAT

Figure 4:
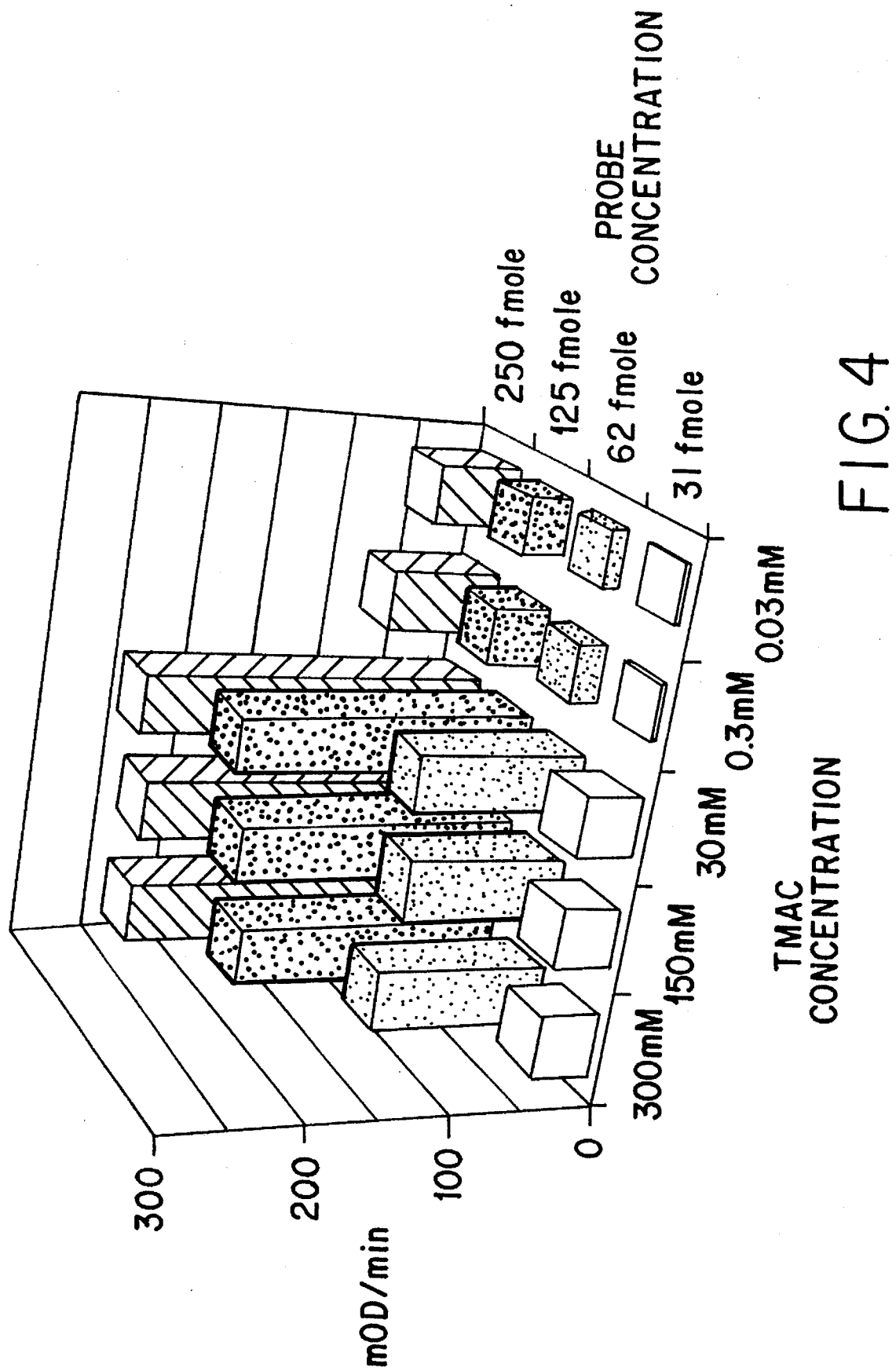
FIG. 4 illustrates the effect of TMAC concentration on the binding of an oligonucleotide to polystyrene.
Figure 5:
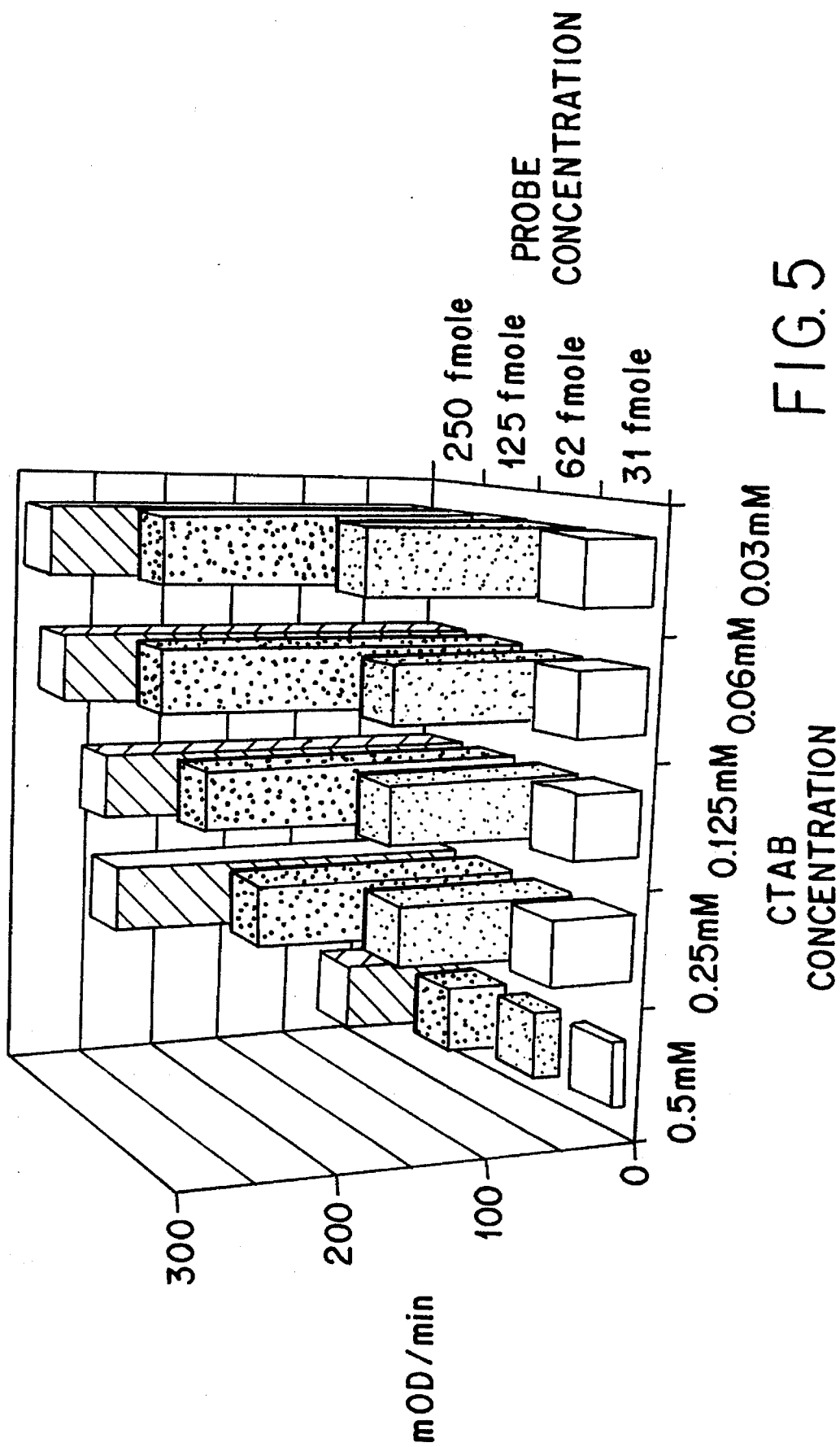
FIG. 5 illustrates the effect of CTAB concentration on the binding of an oligonucleotide to polystyrene.

The presence of biotin was then detected by an enzyme-linked assay. The results obtained (expressed as $mOD_{450}$/min) are represented graphically in FIGS. 4 and 5. For CTAB, best results were seen at the lowest concentration tested (0.03 mM), whereas almost no immobilization was detected at 0.5 mM. For $(CH_3)_4NCl$, the results are exactly opposite: best results were obtained when the reagent was used at relatively high concentrations (300, 150, and 30 mM), with the signals decreasing dramatically at 0.3 and 0.03 mM. This example illustrates how $(CH_3)_4NCl$ behaves like a salt (maximum binding at high concentration) probably due to the low hydrophobicity of its short methyl arms. CTAB, on the other hand, exhibited typical cationic detergent behavior (maximum binding at low concentration), due to its ability to act as a bridge molecule between the hydrophobic plastic and the charged phosphates of the oligonucleotide.]

EXAMPLE 3

Preferred Procedure for Immobilizing Oligonucleotides to 96 Well Polystyrene Plates Using EDC One hundred μl of a 10 μM aqueous solution of the oligonucleotide to be immobilized was mixed with 4.4 ml of distilled water. To this solution was added 500 μl of a 38 mg/ml solution of EDC in water. Fifty μl aliquots of the resulting oligonucleotide solution were added into each well of a polystyrene microtiter plate and incubated overnight at room temperature. Then, the plates were washed three times with a solution containing 10 mM Tris-HCl, pH 7.5, 150 mM NaCl, and 0.05% (v/v) Tween 20 (this solution is abbreviated as TNTw henceforth).

EXAMPLE 4

Preferred Procedure for Immobilizing Oligonucleotides to 96 Well Polystyrene Plates Using NaCl As above, 100 μl of a 10 μM aqueous solution of the oligonucleotide to be immobilized was mixed with 4.4 ml of distilled water. To this solution was added 500 μl of a 5M NaCl solution in water (final concentration of NaCl: 500 mM). Incubation and washing steps were as described above for the EDC immobilization.

EXAMPLE 5

Stability of the Immobilized Oligonucleotides And Efficiency Of Immobilization Of Oligonucleotides To Polystyrene Plates Using Different Immobilization Conditions The immobilization of oligonucleotide #1129 was studied. After overnight incubation, the plate was washed with TNTw. Then, some of the wells were treated with a 0.1N NaOH solution for one hour at room temperature, and then the plates were assayed for the presence of biotin. In a parallel experiment, the unlabeled oligonucleotide #308:

SEQ ID NO:5 5'-AGCCTCAGACCGCGTGGTGC-CTGGT which is complementary to oligonucleotide #1129, was attached under the same set of conditions. This was then followed by hybridization to oligonucleotide #1129, with and without a previous NaOH treatment of the plate. The results (given in $mOD_{450}$/min.) are summarized in Table 2.

TABLE 2

| Expt. | Conditions of Immobilization | No NaOH Treatment of Plate | After NaOH Treatment of Plate |
|---|---|---|---|
| Immobilization of Oligonucleotide #1129 on 96 Well Polystyrene Plates | | | |
| A | water | 35 | 40 |
| B | 150 mM NaCl | 240 | 240 |
| C | 250 mM NaCl | 300 | 320 |
| D | 500 mM NaCl | 275 | 290 |
| E | 50 mM Octyldime-thylamine hydro-chloride, pH 7.0 | 260 | 240 |
| F | 30 mM EDC | 290 | 260 |
| G | 10 mM Tris HCl, 150 mM NaCl, pH 7.5 | 230 | 250 |
| H | TNTw | 1 | 1 |
| Hybridization of Oligonucleotide #1129 to #308 on 96 Well Polystyrene Plates (500 fmol/well) | | | |
| A | water | 3 | 1 |
| B | 50 mM NaCl | 80 | 70 |
| C | 250 mM NaCl | 120 | 95 |
| D | 500 mM NaCl | 130 | 100 |
| E | 50 mM Octyldime-thylamine hydro-chloride, pH 7.0 | 130 | 95 |
| F | 30 mM EDC | 110 | 100 |
| G | 10 mM Tris HCl, 150 mM NaCl, pH 7.5 | 85 | 55 |
| H | TNTw | 1 | 1 |

The results from this experiment showed that the immobilization of the oligonucleotides required the presence of salt. The immobilization was very inefficient in salt-free aqueous solutions. Also, in the presence of Tween-20, no immobilization took place. This was probably due to an "inactivation" of the plate surface by the preferential adsorption of this detergent molecule. Similarly, no immobilization could be achieved if the plate were washed with a solution containing Tween 20 before the attachment step, even if the attachment solution did not contain the detergent. The use of 250 mM NaCl in the attachment step resulted in slightly higher signals in the subsequent hybridization assay.

A number of different commercially available 96 well plates were tested for their suitability for oligonucleotide immobilization. In general, plates that are described as having a more hydrophilic surface gave good results, whereas those with a hydrophobic surface were found unsuitable. Example of suitable plates include Immulon 4 (Dynatech); Maxisorp (Nunc); and ImmunoWare plates (Pierce). No attachment could be achieved on Immulon 1 (Dynatech) and Polysorp (Nunc) plates. All experiments described below have been carried out with Immulon 4 plates.

EXAMPLE 6

Evidence Against Covalent Binding In The Presence Of EDC

EDC (1-ethyl-3-(3-dimethylaminoethyl)carbodiimide HCl) is a well-known crosslinking reagent. For example, it is widely used in peptide synthesis to accomplish the formation of peptide bonds. Therefore, it was important to provide experimental evidence for or against the formation of covalent bonds between the oligonucleotides and any functional groups that might be present on the surface of the polystyrene plates.

Two different types of polystyrene plates were used in this experiment. The first type were Immulon 4 plates, obtained form Dynatech (Chantlily, Va.), and the second type were carboxylate-modified plates from Costar (Cambridge, Mass.). The latter type of plates have been specially designed for covalent binding of biomolecules, mainly peptides and proteins, that do not bind well by simple passive adsorption. Due to the presence of the carboxylate groups on the surface of the Costar plates, the covalent attachment can be carried out using reagents like the water-soluble carbodiimide, EDC. In the following experiment, two oligonucleotides were used, #680 and its 5'-amino-modified version, #680 "amino". The sequence of both oligonucleotides was the same:

SEQ ID NO:6 5'-X-GAGATTCAGCTCTAAGTGCT-GTGGG whereby X denotes a primary amino group in the case of the oligonucleotide #680 "amino". These two oligonucleotides were attached to the Costar and Immulon 4 plates using EDC, exactly as described in Example 3. Two different EDC solutions in water were used. The first was a freshly prepared one, whereas the second one was an aqueous solution of the same concentration that has been kept at room temperature for 15 days. The carbodiimide functional group of EDC is moisture-sensitive, being relatively rapidly hydrolyzed to the corresponding N,N'-disubstituted urea analog upon contact with water. This hydrolysis product of EDC is not capable of acting as a condensing reagent. Thus, the use of this EDC solution in the attachment experiment was designed to show whether the carbodiimide functional group of this compound plays a role in the oligonucleotide immobilization.

Following the immobilization of the two oligonucleotides, the plates were washed with TNTw. Then, 20 μl aliquots of solutions of either of the following synthetic oligonucleotides were added to the wells of both plates and allowed to hybridize to the immobilized oligonucleotides #1209 and 1210 (respectively SEQ ID NO:7 and SEQ ID NO:8):

SEQ ID NO:7 5'-TGCAGCCCACAGCACTTAGAGCT-GAATCTC

SEQ ID NO:8 5'-TGCAACCCACAGCACTTAGAGCT-GAATCTC

Each 20 μl aliquot contained 250 fmole of the corresponding oligonucleotide, in 1.5M NaCl, 10 mM EDTA. The hybridization was allowed to proceed for 30 min at room temperature, whereupon the plates were washed again with TNTw.

Next, an enzymatic extension reaction was carried out, exactly as described in Example 11A (see below). The use of the synthetic oligonucleotides #1209 and #1210 as templates in the extension was expected to lead to the extension of the 3'-end of the immobilized primers by a biotin-labeled ddCTP in the case of oligonucleotide #1209, and a biotin-labeled ddTTP in the case of oligonucleotide #1210. The detection of the incorporated ddNTP was carried out as described below (see Example 11A). The results obtained in the colorimetric assay are summarized in Table 3 which shows the role of the water-soluble carbodiimide, EDC, in oligonucleotide immobilization to two different polystyrene plates. The oligonucleotides #680 and #680 "amino" were immobilized to carboxylate-modified plates (Costar) and Immulon 4 plates (Dynatech). The immobilized oligonucleotides were hybridized to the synthetic templates #1209 and #1210, and subjected to a template-directed enzymatic extension at their 3'-ends (GBA™) Biotin-labeled ddNTPs were used. The results are given as $mOD_{450}$/min.

TABLE 3

| | Detection of the Incorporation of ddNTP | | | | |
|---|---|---|---|---|---|
| Attachment Conditions of Primer | Synthetic Template Used | Costar Plate Base | | Immulon 4 Plate Base | |
| | | C | T | C | T |
| | Fresh EDC | | | | |
| #680 | 1209 | 130 | 12 | 290 | 10 |
| #680 | 1210 | 7 | 140 | 3 | 185 |
| #680 Amino | 1209 | 155 | 11 | 295 | 8 |
| #680 Amino | 1210 | 6 | 130 | 6 | 200 |
| | "Old" EDC | | | | |
| #680 | 1209 | 8 | 7 | 7 | 250 |
| #680 | 1210 | 6 | 8 | 3 | 160 |
| #680 Amino | 1209 | 5 | 4 | 310 | 8 |
| #680 Amino | 1210 | 8 | 4 | 4 | 195 |

The main results from this experiment can be summarized as follows:

1. Oligonucleotides can be immobilized to carboxylate-modified Costar plates using fresh carbodiimide as the condensing reagent. Both oligonucleotides containing a primary amine function at the 5'-end and those without it can be immobilized. It is very likely that the attachment takes place at least partially via the exocyclic amino groups of the heterocyclic bases. The immobilized oligonucleotides can be used in hybridization-based DNA assays. The immobilization only takes place in the presence of fresh EDC; no attachment takes place when the EDC used has hydrolyzed.

2. Under similar conditions, oligonucleotides can be successfully immobilized to Immulon 4 plates and used in hybridization-based assays. In contrast to the Costar plates, however, both a freshly prepared and a hydrolyzed EDC solution give virtually identical results. The EDC is thus not acting as a covalent binding reagent in this case.

EXAMPLE 7

Detection of PCR products in polystyrene plates

Oligonucleotides immobilized on polystyrene plates (or microscope glass slides, see below) can be used as probes in a new, non-radioactive, solid-phase assay of polymerase chain reaction (PCR) products. The method can be fully automated, and a very high throughput can be achieved. It comprises four individual steps:

1. DNA amplification by PCR, using one regular and one labeled, phosphorothioate-modified primer;
2. conversion of the double-stranded PCR product into the single-stranded form;
3. hybridization of the single-stranded PCR product to the oligonucleotide probe that has been immobilized to the solid phase;
4. colorimetric detection of the PCR product in an ELISA-type assay.

These individual steps are described in more detail in the example that follows. In this example, 96 well polystyrene ELISA plates (Immulon 4, obtained from Dynatech, Chantlily, Va.) were used.

The following PCR amplification illustrates the application of the present invention to PCR amplification. Horse genomic DNA was the source of DNA in all PCR amplifications reactions. PCR reactions were carried out in a total volume of 50 µl. The final concentration of the PCR primers was 0.5 µM. Following an initial two minute denaturation step at 95° C., thirty-five cycles were carried out, each consisting of denaturation (1 min at 95° C.), annealing (2 min at 60° C.), and extension (3 minutes at 72° C.). Taq DNA polymerase was obtained from Perkin-Elmer and used at a concentration of 0.025 u/µl. The final composition of the PCR buffer was: 1.5 mM MgCl$_2$, 50 mM KCl, 10 mM Tris-HCl, pH 8.3, and 200 µg/ml BSA. The sequences of the PCR primers used are given below. The lengths of the PCR products are also provided. Phosphorothioate bonds are located between the underlined and highlighted nucleotides. Note that the 5'-terminal biotin residue is also attached through a phosphorothioate bond.

A: 93 bp PCR amplification product:
   PCR Primers:
     SEQ ID NO:9 5'-B-CCAAAGGAGCTGGGTCTGAAA-CAAA
     SEQ ID NO:10 5'-ATGGCTTCCCACCCTACCCATC-CCG
   Capture probe:
     SEQ ID NO:11 5'-TGTTCTGGGAAAGACCACAT-TATTT
B: 201 bp PCR amplification product:
   PCR Primers:
     SEQ ID NO:12 5'-B-ATGCTCCCAGGTGATTCCAGT-GTGC
     SEQ ID NO:13 5'-GGTGCTGTGCGAGGTACACT-TGACTG
   Capture probe:
     SEQ ID NO:14 5'-AGAAACACAAGGCCCAAGAA-CAGGA
C: 547 bp PCR amplification product:
   PCR Primers:
     SEQ ID NO:15 5'-B-GGATCCAGATGAACAACCA-GATGAA
     SEQ ID NO:16 5'-CTGCAGCCCACTGGGCCT-TCTTTGT
   Capture probe:
     SEQ ID NO:17 5'-CCTTTGTGTAGAGTAGTTCAAG-GAC Aliquots of the PCR reactions were withdrawn after the amplification and analyzed by polyacrylamide gel electrophoresis.

EXAMPLE 8

Preparation of Single-Stranded PCR Products

In order to protect one of the strands of the double-stranded PCR product from exonuclease hydrolysis, four phosphorothioate bonds were introduced during synthesis at the 5'-end of one of each pair of the PCR primers. For generation of single-stranded PCR products, following the PCR amplification, T7 gene 6 exonuclease was added to a final concentration of 2 units/µl of PCR reaction. Incubation was for one hour at room temperature. The T7 gene 6 exonuclease was purchased from USB and diluted in a buffer recommended by the manufacturer. Following the exonuclease treatment, aliquots of the reaction mixtures were withdrawn and analyzed by polyacrylamide gel electrophoresis.

EXAMPLE 9

Hybridization Of Single-Stranded PCR Fragments To Oligonucleotides Immobilized In ELISA Plates After The exonuclease treatment, an equal volume of 3M NaCl, 20 mM EDTA was added to the reaction mixture and 20 µl aliquots of the resulting solution transferred to individual wells containing the appropriate immobilized oligonucleotide molecule. The sequences of the immobilized capture probes are given above. These capture probes were immobilized using 500 mM NaCl. Hybridization was carried out for 30 min at room temperature and was followed by washing with TNTw.

EXAMPLE 10

Colorimetric Detection

After the hybridization, the plate was incubated with a 1:1200 dilution of anti-biotin horseradish peroxidase conjugate (Vector Laboratories, Burlingame, Calif.) in 1% BSA in TNTw, for 30 min at room temperature. The plate was then washed six times with TNTw and a solution of 1 mg/ml of o-phenylenediamine (OPD) in 0.1M citrate buffer, pH 4.5, containing 0.012% H$_2$O$_2$ was added. The plate was immediately placed in a plate reader (V$_{max}$, Molecular Devices), and the development of color was followed at 450 nm for 2 min. Table 4 shows the results (expressed as mOD$_{450}$/min) of microtiter plate hybridization assays of the PCR reactions A, B, and C. The products of PCR reactions A, B, and C were rendered single-stranded by treatment with 2 u/µl of T7 gene 6 exonuclease and aliquots corresponding to 5 µl of the initial PCR reaction were added to the wells of a microtiter plate containing the appropriate capture oligonucleotides for hybridization. The capture oligonucleotides were immobilized to the plate using 500 mM NaCl. The results of the colorimetric assay are presented in mOD$_{450}$/min. All experiments were carried out in duplicate; the results shown are averages (NT=not tested).

TABLE 4

Analysis of Plate Hybridization Assays Using Immobilized Capture Oligonucleotides

| PCR Reaction | Hybridization to Capture Oligonucleotide for Reaction | Signal Without Exonuclease Treatment | Signal After Exonuclease Treatment (2 u/ml) |
|---|---|---|---|
| A | A | 2 | 450 |
| A | B | NT | 3 |
| A | C | NT | 1 |
| A (Neg. Control) | A | NT | 1 |
| B | A | NT | 4 |
| B | B | 1 | 630 |
| B | C | NT | 1 |
| B (Neg. Control) | A | NT | 4 |
| C | A | NT | 3 |
| C | B | NT | 1 |
| C | C | 2 | 450 |
| C (Neg. Control) | A | NT | 4 |

EXAMPLE 11

Figure 3:
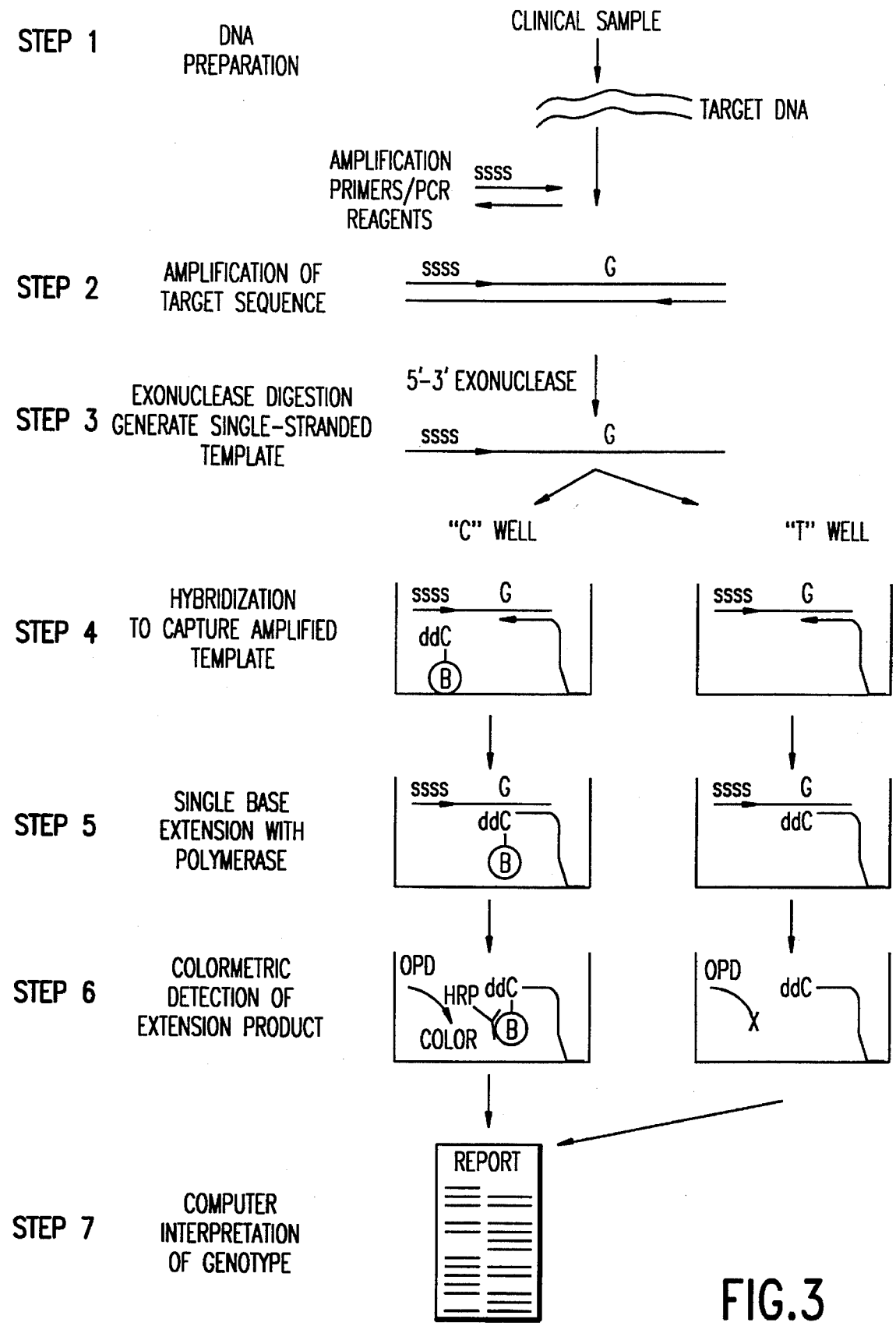
FIG. 3 is a diagram of a GBA™ genetic bit analysis protocol.

Application Of The Solid Phase Immobilization Method For The Non-Radioactive Typing Of Single-Base Nucleic Acid Polymorphisms GBA™ Genetic Bit Analysis is a solid-phase method for the typing of single-nucleotide polymorphisms. The method is illustrated in FIG. 3. Using the method described in the present patent application, oligonucleotide primers can be immobilized on solid phases like polystyrene or glass, hybridized to PCR-derived, single-stranded templates, and subjected to enzymatic extension at their 3'-ends by a single, labeled ddNTP. The nature of the incorporated ddNTP is determined by the nucleotide that is located in the opposite strand (the polymorphic nucleotide). This assay can be conveniently carried out both in polystyrene ELISA plates, or on glass slides.

Three examples of GBA™ genetic bit analysis on polystyrene plates are given below (A, B, and C). In Example 11A, GBA™ genetic bit analysis primers are attached to polystyrene plates by the method of the present invention, and used to type a diallelic polymorphism in equine genomic DNA. The second and the third examples compare the GBA™ analysis results obtained using two different oligonucleotide immobilization approaches. In Example 11A, the oligonucleotide primers (the GBA™ primers) were immobilized to polystyrene plates using the method of the present invention, whereas in Example 11C the immobilization has been carried out by a modification of a previously described method (Running, J. A. et al., *Biotechniques* 8: 276–277, 1990). The latter method is known to afford covalent attachment of the oligonucleotides via their 5'-ends to the poly-(Lys, Phe)-coated plate. As can be seen from Example 11B and Example 11C, the method of the present invention for oligonucleotide immobilization is significantly simpler to perform than the method of Running and Urdea, yet the results seen in the GBA™ analysis (as expressed by the signal-to-noise ratios of the individual bases) are significantly better when the immobilization has been carried out by the method of the present invention.

EXAMPLE 11A

Typing Of DNA Single-Base Polymorphisms By GBA™ Analysis: The Use Of PCR-Derived Templates And Primers Immobilized To Polystyrene By The Method Of The Present Invention The PCR primers (#1833 and #1834, respectively) used to amplify a 112 bp region from equine genomic DNA that contains a single-base polymorphism had the following sequences:

SEQ ID NO:18 5'-ATAATACAGAAGTTCTGAGAGGCTA

SEQ ID NO:19 5'-GGATCCAGGTCTGCTTCTGCTTCCC

Note that the PCR primer #1834 contains four phosphorothioate bonds at its 5'-end. These protect this end of the double-stranded PCR product from the exonucleolytic action of the T7 gene 6 exonuclease and allow the preparation of single-stranded PCR product.

The PCR amplification was carried out as described in Example 7. Genomic DNA isolated form four different horses was used. The double-stranded PCR product was converted to the single-stranded form as described in Example 8, and it was hybridized to the GBA™ primer #814 as described in Example 9. The GBA™ primer had the following sequence:

SEQ ID NO:20 5'-AAGAGAAAGAGTTTTGCCTCAATCC

The immobilization of this GBA™ primer to a polystyrene plate was carried out with NaCl, as described in Example 4.

Following the hybridization of the PCR-derived, single-stranded DNA fragment to the immobilized GBA™ primer, the 3'-end of the latter was enzymatically extended by one labeled ddNTP, in the presence of the large fragment of DNA polymerase I from *E. coil* (Klenow polymerase). The extension mixture used contained the following components: 20 mM Tris-HCl, pH 7.5; 10 mM $MgCl_2$; 25 mM NaCl; 10 mM $MnCl_2$; 15 mM sodium isocitrate; 1.5 µM of each of three unlabeled 2',3'-dideoxynucleoside 5'-triphosphates and 1.5 µM of one biotin-labeled 2',3'-dideoxynucleoside 5'-triphosphate; and 0.15 units of the Klenow polymerase. The presence of biotin was then revealed by a colorimetric detection as described in Example 10. The results are shown in Table 5. These results show that, for this polymorphism, horses 1 and 3 are heterozygotes, horse 2 is a G homozygote, and horse 4 is an A homozygote.

TABLE 5

Results of the GBA ™ Analysis Experiment

| Horse | Base A | Base G |
| --- | --- | --- |
| 1 | 115 | 80 |
| 2 | 2 | 150 |
| 3 | 75 | 90 |
| 4 | 85 | 1 |

EXAMPLE 11B

GBA™ Analysis On Polystyrene Plates Using Primers Immobilized By The Method Of The Present Invention: Comparison Of Two Different Methods For Oligonucleotide Immobilization The following GBA™ primer (#670) was immobilized to polystyrene plates as described in Example 1. The sequence of this primer is

SEQ ID NO:21 5'-TGTTCTGGGAAAGACCACATTATTT

Then, this immobilized GBA™ primer was hybridized to the following two synthetic oligonucleotides (#1241 and #1242). The respective sequences of these oligonucleotides are:

SEQ ID NO:22 5'-GAACAAAATAATGTGGTCTTTCCCAGAACA

SEQ ID NO:23 5'-GAACTAAATAATGTGGTCTTTCCCAGAACA

After the hybridization, the immobilized GBA™ primer was enzymatically extended at its 3' end as described in Example 9A. The colorimetric detection was carried out as described in Example 8. The signals obtained for the individual bases in the colorimetric assay are presented in Table 6.

TABLE 6

Results of the GBA ™ Experiment (mOD/min)

| Oligonucleotide | Base A | Base T | Base C | Base G |
| --- | --- | --- | --- | --- |
| #1241 | 45 | 160 | 1 | 1 |
| #1242 | 160 | 1 | 1 | 1 |

EXAMPLE 11C

GBA™ Analysis On Polystyrene Plates Using Primers Immobilized By A Modification Of The Method Of Running et al.: Comparison Of Two Different Methods For Oligonucleotide Immobilization The oligonucleotide #1592 was used as the GBA™ primer. This oligonucleotide has the same sequence as #670 (see Example 9B), but is modified with a thiophosphate group at its 5'-end. This thiophosphate group is used as a reactive handle in the subsequent covalent immobilization to the poly-(Lys, Phe)-coated plate. To introduce this thiophosphate group, a 5'-phosphate-on phosphoramidite (obtained from Glen Research) was coupled to the 5'-end of the oligonucleotide during its synthesis. The oxidation during the coupling of this phosphoramidite was replaced by a sulfurization, thereby creating the desired 5'-thiophosphate. The reagent used for the sulfurization was tetraethylthiuram disulfide (TETD), obtained from Applied Biosystems. Immediately before the immobilization to the polystyrene plates, this modified oligonucleotide was reacted with a solution of 4-nitrophenyl bromoacetate, a heterobifunctional crosslinker, in a mixture of DMSO and phosphate buffer, pH 7.2. The course of the modification reaction was followed by HPLC and after its completion the reaction mixture was passed through a NAP5 gel filtration column (Pharmacia) in order to remove the excess crosslinking reagent. This activated oligonucleotide was then immediately used in the immobilization step since the reactive ester group at its 5'-end hydrolyzes upon storage.

The polystyrene plates used for the immobilization were coated by passive adsorption of poly-(Lys, Phe) as described (Running, J. A. and Urdea, M. S., *Biotechniques* 8: 276–277, 1990). After washing, aliquots containing 50 pmoles of the activated, modified oligonucleotide #1592 in phosphate buffer, pH 7.2 were delivered to each well and incubated overnight. The plates were then washed with TNTw, 0.1N NaOH, and again with TNTw, before the hybridization to the oligonucleotides #1241 and #1242. All subsequent steps (hybridization, extension, and colorimetric detection) were carried out as described above. The results are in Table 7.

TABLE 7

Results of the GBA ™ Experiment (mOD/min)

| Oligonucleotide | Base A | Base T | Base C | Base G |
| --- | --- | --- | --- | --- |
| #1241 | 90 | 150 | 15 | 35 |
| #1242 | 133 | 30 | 15 | 10 |

EXAMPLE 12

Immobilization Of Oligonucleotides To Glass Slides And Hybridization Assay On Slides Oligonucleotide #308 was used in this experiment. The sequence of this oligonucleotide is:

SEQ ID NO:5 5'-AGCCTCAGACCGCGTGGTGC-CTGGT

For the attachment of the oligonucleotide to the glass slides, the following solution was prepared: 1.1 ml $H_2O$, 25 µl of a 10 µM solution of the oligonucleotide #308 in water, and 125 µl of a 38 mg/ml solution of EDC in water. As a control, another mixture was prepared that did not contain EDC: 1.225 µl $H_2O$ and 25 µl of the 10 µM oligonucleotide solution. Twenty µl aliquots of these solutions (containing 4 pmoles of oligonucleotide) were delivered to the individual "wells" of a glass slide (obtained from Cel-Line); the diameter of each "well" on the slides was 4 mm. The individual "wells" are separated from each other by a thin hydrophobic Teflon coating. The incubation was overnight at room temperature, at a 100% relative humidity in order to prevent evaporation. Following this incubation, the slides were washed three times by dipping them into a solution of 10 mM Tris-HCl, pH 7.5, 150 mM NaCl, 0.05% Tween 20 (TNTw). The slides were then allowed to air dry before the hybridization step.

For hybridization, two 5'-biotinylated oligonucleotides were used: #1129, which has a sequence complementary to that of #308, and #431, which is not complementary to #308. The respective sequences of these two oligonucleotides are ("B" represents biotin):

SEQ ID NO:1 5'-B-ACCAGGCACCACGCGGTCT-GAGGCT

SEQ ID NO:24 5'-B-AGCCTCAGACCGCGTGGTGC-CTGGT

These two oligonucleotides were added to separate "wells" on the slide. Twenty µl aliquots of solutions of these oligonucleotides in 1.5M NaCl, 10 mM EDTA were added to separate "wells" of the slide, and the hybridization was allowed to proceed for 30 min at room temperature, at 100% relative humidity.

Following the hybridization, the slides were washed again in the same manner as described above in TNTw. After drying, twenty µl aliquots of a 1:1000 dilution of a horseradish peroxidase (HRP)-conjugated antibiotin in 1% BSA in TNTw were added to each "well" and incubated for 30 min as described above. Then the slides were washed six times with TNTw as described above and air dried. A colorimetric reaction was then carried out to reveal the presence of biotin. A ready-to-use HRP substrate solution (obtained from Pierce) was used. Twenty µl aliquots of this substrate solution were added to each "well" and the color development followed visually.

In this experiment, the development of an intense blue color was observed in those wells where the biotinylated oligonucleotide #1129 had been hybridized to the oligonucleotide #308, and where the latter oligonucleotide had been attached to the slide in the presence of EDC. No color development was observed where the oligonucleotide #308 has been immobilized in the absence of EDC. Also, no color development was observed where the oligonucleotide #431 has been hybridized to the oligonucleotide #308, regardless of the manner of attachment of the latter oligonucleotide.

Alternatively, in order to obtain more quantitative results, following an incubation with the colorimetric substrate for a suitable period of time, the substrate solution was removed from the "wells", transferred to the wells of a standard 96 well plate, mixed with 100 µl of $H_2O$ and 50 µl of 3M $H_2SO_4$ and the absorbance of the solution recorded in a 96 well plate reader, at 450 nm. The results of this experiment are shown in Table 8.

TABLE 8

Results of the GBA ™ Experiment (mOD/min)

| Oligonucleotide | Attachment | Hybridized To | $A_{450}$ |
|---|---|---|---|
| #308 | with EDC | #1129 | 0.240 |
| #308 | with EDC | #431 | 0.055 |
| #308 | without EDC | #1129 | 0.050 |

EXAMPLE 13

GBA™ Analysis On Microscope Slides

The following is an example of GBA™ on glass slides. The glass slides used were obtained from Cel-Line Associates, Inc., Newfield, N.J. The GBA™ primer used in this experiment was oligonucleotide #670 (see Example 11B). The immobilization of this primer was carried out as described above, using EDC. In the hybridization step, 100 fmoles of the synthetic templates #1241 and #1242 were added per "well" of the slide. The hybridization buffer contained 1.5M NaCl and 10 mM EDTA. Following the hybridization, the slides were washed in TNTw and then the primer extension was carried out. The composition of the extension solution was as described in Example 11A. Twenty μl of this solution was added per "well", and the reaction allowed to proceed for 5 min at room temperature. After washing with TNTw, the presence of a biotinylated ddNTP was assayed for as described above in Example 12. The endpoint readings obtained are in Table 9.

TABLE 9

Results of the GBA ™ Experiment ($A_{450}$)

| Template | Base T | Base A |
|---|---|---|
| #1241 | 0.274 | 0.077 |
| #1242 | 0.076 | 0.310 |

The above experiments demonstrate that relatively short, unmodified oligonucleotides can be efficiently immobilized onto the surface of hydrophilic polystyrene or glass simply by incubation in a solution containing an inorganic salt, such as NaCl, or a cationic detergent, such as octyldimethylamine hydrochloride. The simplicity of this invention should allow the deposition of polynucleotides onto glass or polystyrene substrates in a wide variety of ways. Pattern-specific deposition should be possible using silk-screening and ink-jet technologies, as well as photolithography to mask areas of the substrate to prevent oligonucleotide binding. The microdeposition of oligos, using the above technologies, could allow miniaturized assays with a vast increase in the number of analytes that could be detected simultaneously and a corresponding decrease in the cost of labor and reagents.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:
1. A method for non-covalently immobilizing a synthetic nucleic acid molecule on a solid support which is a hydrophilic polystyrene solid support containing a hydrophilic group selected from the group consisting of —OH, —C=O, and —COOH, or a glass solid support, said method comprising the steps:
  (a) contacting said support with a solution having a pH of from about 6 to about 8, and containing said nucleic acid and (1) a cationic detergent selected from the group consisting of 1-ethyl-3-(3'-dimethylaminopropyl)-1,3-carbodiimide hydrochloride provided at a concentration of from about 30 mM to about 100 mM, and octyldimethylamine hydrochloride provided at a concentration of from about 50 mM to about 150 mM or (2) NaCl provided at a concentration of from about 50 mM to about 250 mM, to thereby non-covalently immobilize said nucleic acid to said support, wherein:
  (i) when said cationic detergent is 1-ethyl-3-(3'-dimethylaminopropyl)carbodiimide-1,3-hydrochloride, said support is selected from the group consisting of glass or said hydrophilic polystyrene;

(ii) when said cationic detergent is octyldimethylamine hydrochloride, said support is said hydrophilic polystyrene; and (iii) when said solution contains said NaCl, said support is said hydrophilic polystyrene; and (b) subsequently washing said solid support with an aqueous solution.

2. The method of claim 1, wherein said solid support is said hydrophilic polystyrene support.

3. The method of claim 1, wherein said solid support is said glass support.

4. The method of claim 1, wherein said solid support is in the form of a bead or membrane.

5. The method of claim 1, wherein said cationic detergent is 1-ethyl-3-(3'-dimethylaminopropyl)-1,3-carbodiimide hydrochloride.

6. The method of claim 1, wherein said cationic detergent is octyldimethylamine hydrochloride.

7. The method of claim 1, wherein in step (b), said aqueous solution contains a non-ionic detergent.

8. The method of claim 7, wherein said non-ionic detergent is polyoxyethylene (20) sorbitan.

9. The method of claim 8, wherein said polyoxyethylene (20) sirbitan is provided in a solution that additionally contains buffered saline.

10. The method of claim 1, wherein said synthetic nucleic acid molecule is an oligonucleotide having a minimum length of at least 12 nucleotide residues and a maximum length of about 100 residues.

11. The method of claim 10, wherein said oligonucleotide is chemically modified.

12. The method of claim 2, wherein said hydrophilic polystyrene support is in the form of a 96-well microtiter plate.

13. The method of claim 2, wherein said hydrophilic polystyrene support is in the form of a 96-pin array designed to fit into a 96-well microtiter plate.

14. The method of claim 3, wherein said glass support is in the form of a microscope slide.

15. The method of claim 1, wherein said immobilized synthetic nucleic acid molecule is a polynucleotide and wherein said method additionally comprises the steps of:

(A') capturing from solution at least one strand of a specific polynucleotide analyte by hybridization to said immobilized polynucleotide; and (B') detecting the presence of the captured analyte.

16. The method of claim 1, wherein said immobilized synthetic nucleic acid molecule is a polynucleotide and wherein said method additionally comprises the steps of:

(A") amplifying a specific region of a specific genome using a polymerase chain reaction to produce an amplified specific region of said genome, said region having a sequence complementary to said immobilized polynucleotide; and (B") capturing from solution at least one strand of said amplified specific region of said genome by hybridization to said immobilized polynucleotide; and (C") detecting the presence of said specific region of said genome.

17. The method of claim 1, wherein said immobilized synthetic nucleic acid molecule is a polynucleotide primer and wherein said method additionally comprises the steps of:

(A''') incubating a sample of nucleic acid of a target organism, containing a single nucleotide polymorphism in the presence of said immobilized polynucleotide primer and a polymerase and at least one dideoxynucleotide derivative, under conditions sufficient to permit a polymerase mediated, template-dependent extension of said primer, said extension causing the incorporation of a single dideoxynucleotide derivative that is complementary to a polymorphic nucleotide of said single nucleotide polymorphism of said target organism nucleic acid;

(B''') permitting said template-dependent extension of said primer molecule, and said incorporation of said single dideoxynucleotide; and (C''') determining the identity of the dideoxynucleotide derivative incorporated that is complementary to said polymorphic nucleotide.

18. The method of claim 1, wherein said solid support is in the form of a filter.

19. The method of claim 1, wherein said solid support is in the form of an affinity column.

* * * * *